US012616724B2

(12) United States Patent
Chin

(10) Patent No.: US 12,616,724 B2
(45) Date of Patent: May 5, 2026

(54) PHARMACEUTICAL COMPOSITION FOR PREVENTING OR TREATING INTESTINAL DAMAGE COMPRISING *LEUCONOSTOC CITREUM* STRAIN AS ACTIVE INGREDIENT

(71) Applicant: LISCURE BIOSCIENCES CO., LTD., Seongnam-si (KR)

(72) Inventor: Hwa Sup Chin, Yongin-si (KR)

(73) Assignee: LISCURE BIOSCIENCES CO., LTD., Seongnam-si (KR)

( * ) Notice: Subject to any disclaimer, the term of this patent is extended or adjusted under 35 U.S.C. 154(b) by 296 days.

(21) Appl. No.: 18/276,154

(22) PCT Filed: Feb. 7, 2022

(86) PCT No.: PCT/KR2022/001870
§ 371 (c)(1),
(2) Date: Aug. 7, 2023

(87) PCT Pub. No.: WO2022/169337
PCT Pub. Date: Aug. 11, 2022

(65) Prior Publication Data
US 2024/0091281 A1     Mar. 21, 2024

(30) Foreign Application Priority Data

Feb. 8, 2021     (KR) ........................ 10-2021-0017813
Feb. 4, 2022     (KR) ........................ 10-2022-0014825

(51) Int. Cl.
*A61K 39/02*     (2006.01)
*A61K 35/744*     (2015.01)
*A61P 1/00*     (2006.01)
*C12N 1/205*     (2026.01)

(52) U.S. Cl.
CPC .............. *A61K 35/744* (2013.01); *A61P 1/00* (2018.01); *C12N 1/205* (2021.05)

(58) Field of Classification Search
None
See application file for complete search history.

(56) References Cited

U.S. PATENT DOCUMENTS

2019/0030097 A1     1/2019  Kim et al.
2022/0047652 A1     2/2022  Choi et al.

FOREIGN PATENT DOCUMENTS

| CN | 107412272 A | 12/2017 |
|---|---|---|
| KR | 10-0808910 B1 | 3/2008 |
| KR | 10-1302465 B1 | 9/2013 |
| KR | 10-1937365 A | 1/2019 |
| KR | 10-2032982 B1 | 10/2019 |
| KR | 10-2038695 B1 | 10/2019 |
| KR | 10-2020-0128887 A | 11/2020 |
| KR | 10-2201517 B1 | 1/2021 |
| WO | 2020/175940 A1 | 9/2020 |

OTHER PUBLICATIONS

Written Opinion for PCT/KR2022/001870, dated May 12, 2022.
International Search Report for PCT/KR2022/001870, dated May 12, 2022.
Extended European Search Report issued Jan. 24, 2025 in European Application No. 22750086.5.
Silva et al: "Probiotic properties of *Weissella cibaria* and *Leuconostoc citreum* isolated from *tejuino*—A typical Mexican beverage", LWT—Food Science and Technology, vol. 86, Aug. 3, 2017, pp. 227-232 (6 Pages total).
Ferreira et al: "Oral Supplementation of Butyrate Reduces Mucositis and Intestinal Permeability Associated with 5-Fluorouracil Administration", LIPIDS, vol. 47, May 31, 2012 , pp. 669-678 (10 Pages total).
Han et al: "Sodium butyrate protects the intestinal barrier function in peritonitic mice", Int J Clin Exp Med 2015, vol. 8, No. 3, Mar. 30, 2015, pp. 4000-4007 (8 Pages total).
Office Action issued Oct. 7, 2025 in Japanese Application No. 2023-547880.

*Primary Examiner* — Jennifer E Graser
(74) *Attorney, Agent, or Firm* — Sughrue Mion, PLLC

(57)     ABSTRACT

The present invention relates to a composition comprising a *Leuconostoc citreum* strain or a culture thereof as an active ingredient for preventing, improving or treating intestinal damage, specifically intestinal damage caused by inflammatory bowel disease, non-alcoholic steatohepatitis or chemotherapy.

According to the present invention, since the composition exhibits excellent preventive and therapeutic effects on various intestinal damages such as inflammatory bowel disease, non-alcoholic steatohepatitis, and chemotherapy, the composition can be usefully used as a composition for the treatment, prevention or improvement of human or animal intestinal damage.

3 Claims, 2 Drawing Sheets

Specification includes a Sequence Listing.

[FIG. 1]
ZO-1
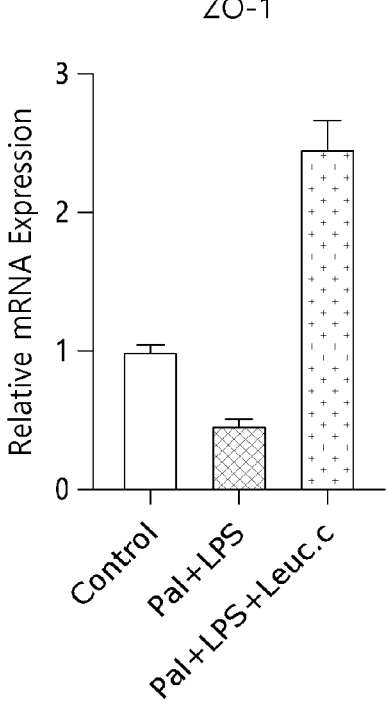
[FIG. 2]
Occludin
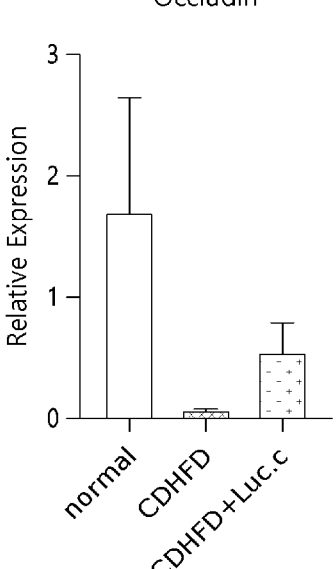

[FIG. 3]
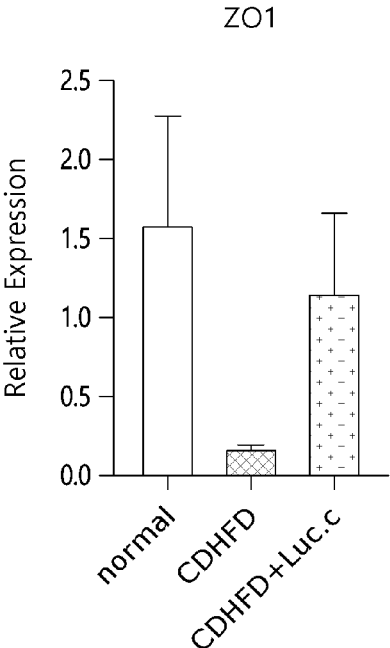

PHARMACEUTICAL COMPOSITION FOR PREVENTING OR TREATING INTESTINAL DAMAGE COMPRISING *LEUCONOSTOC CITREUM* STRAIN AS ACTIVE INGREDIENT

CROSS REFERENCE TO RELATED APPLICATIONS

This application is a National Stage of International Application No. PCT/KR2022/001870 filed Feb. 7, 2022, claiming priority based on Korean Patent Application No. 10-2021-0017813 filed Feb. 8, 2021 and Korean Patent Application No. 10-2022-0014825 filed Feb. 4, 2022, the entire disclosures of which are incorporated herein by reference.

INCORPORATION BY REFERENCE OF SEQUENCE LISTING

The content of the electronically submitted sequence listing, file name: Q289667_sequence listing as filed. TXT; size: 2,376 bytes; and date of creation: Aug. 7, 2023, filed herewith, is incorporated herein by reference in its entirety.

TECHNICAL FIELD

The present invention relates to a composition comprising a *Leuconostoc citreum* strain or a culture thereof as an active ingredient for preventing, improving or treating intestinal damage, specifically intestinal damage caused by inflammatory bowel disease, non-alcoholic steatohepatitis, and chemotherapy.

BACKGROUND ART

As the modern people have undesirable dietary habits and unhealthy lifestyles such as meat-oriented dietary life, instant and processed food-oriented eating habits, excessive intake of stimulating foods, and changes in food intake patterns that have become hasty due to a busy living environment, and get older, harmful bacteria are superior to beneficial bacteria, and the balance of intestinal bacteria is broken, which adversely affects the health of the intestine.

The modern people are exposed to various intestinal diseases, and many people not only suffer from intestinal damage due to diseases such as inflammatory bowel disease, non-alcoholic steatohepatitis, and colorectal cancer, but also have problems in recovery of intestinal damage and maintenance of functions due to intestinal damage even after treatment.

Microbiota refers to a microbial community in an environment as a microbial flora, and it is known that the microbiota plays an important role in maintaining homeostasis of a host, for example, human immunity, metabolites, and the like. The microbiota and the host exchange chemical signals, and the expression of immune cells, the production of neurotransmitters, short chain fatty acids (SCFA), and the like by the microbiota have a hypertrophic effect on a host system, and particularly, probiotics/prebiotics balance the unbalanced microbiota of the host, so that the metabolites of the healthy microbiota may improve the health of the host.

Currently, there are published a composition for preventing or treating alcoholic intestinal damage containing probiotics as an active ingredient (Korean Patent Registration No. 10-2038695) and a composition for improving an intestinal environment containing a novel *Lactobacillus acidophilus* strain (Korea Patent Registration No. 10-2201517), but there is no description about a preventive or therapeutic effect of intestinal damage using a *Leuconostoc citreum* strain as an active ingredient.

Under this background, the present inventors found that a composition containing a *Leuconostoc citreum* strain or a culture thereof, which had little toxicity and side effects, had an effect of treating intestinal damage and restoring functions on the intestine damaged by inflammatory bowel disease, non-alcoholic steatohepatitis, chemotherapy, etc., and then completed the present invention.

DISCLOSURE

Technical Problem

An object of the present invention is to provide a pharmaceutical composition for preventing or treating intestinal damage comprising a *Leuconostoc citreum* strain as an active ingredient.

Further, another object of the present invention is to provide a food composition or food additive composition for preventing or improving intestinal damage including a *Leuconostoc citreum* strain as an active ingredient.

Further, yet another object of the present invention is to provide a feed composition or feed additive composition for preventing or improving livestock intestinal damage including a *Leuconostoc citreum* strain as an active ingredient.

Technical Solution

An aspect of the present invention provides a pharmaceutical composition for preventing or treating intestinal damage including a *Leuconostoc citreum* strain or its culture as an active ingredient.

Further, another aspect of the present invention provides a food composition or food additive composition for preventing or improving intestinal damage including a *Leuconostoc citreum* strain or its culture as an active ingredient.

Further, yet another aspect of the present invention provides a feed composition or feed additive composition for preventing or improving livestock intestinal damage including a *Leuconostoc citreum* strain or its culture as an active ingredient.

Advantageous Effects

An aspect of the present invention provides a pharmaceutical composition for preventing or treating intestinal damage including a *Leuconostoc citreum* strain or its culture as an active ingredient.

Further, another aspect of the present invention provides a food composition or food additive composition for preventing or improving intestinal damage including a *Leuconostoc citreum* strain or its culture as an active ingredient.

Further, yet another aspect of the present invention provides a feed composition or feed additive composition for preventing or improving livestock intestinal damage including a *Leuconostoc citreum* strain or its culture as an active ingredient.

DESCRIPTION OF DRAWINGS

FIG. 1 is a diagram showing a graph of measuring a gene expression level of a ZO1 protein after Caco2 enterocytes are treated with a composition according to the present invention.

FIG. 2 is a diagram showing a graph of measuring a gene expression level of an Occludin protein after treating a composition according to the present invention in a CDHFD mouse model.

FIG. 3 is a diagram showing a graph of measuring a gene expression level of a ZO1 protein after treating a composition according to the present invention in a CDHFD mouse model.

BEST MODE

A composition including a *Leuconostoc citreum* strain of the present invention or its culture as an active ingredient has a preventive or therapeutic effect of intestinal damage, and may be used as a pharmaceutical composition.

The *Leuconostoc citreum* strain of the present invention is a lactic acid bacteria strain. The *Leuconostoc citreum* strain is a probiotic, and has general intestinal regulating and immune enhancing effects of lactic acid bacteria. It is a well-known fact that lactic acid bacteria in *Leuconostoc* sp. have an intestinal regulating effect and an immune enhancing effect.

The *Leuconostoc citreum* strain may be a *Leuconostoc citreum* WiKim0104 strain, and has a nucleic acid sequence represented by SEQ ID NO: 1.

The *Leuconostoc citreum* strain may be inoculated in 0.1 to 10% of a MRS liquid medium and cultured and used at 25 to 37° C. for 4 to 48 hours.

The culturing method is preferably a static culture method, but is not limited thereto.

In the present invention, the 'probiotics' is understood as the meaning of 'a living microorganism that has a beneficial effect on the health of the host by improving an intestinal microbial environment of the host in the gastrointestinal tract of animals, including humans'. The probiotics are live microorganisms with probiotic activity, which may have a beneficial effect on the intestinal flora of the host, when fed to humans or animals in the form of dried cells or fermentation products in the form of single or multiple strains.

The intestinal damage may be intestinal damage caused by inflammatory bowel disease, non-alcoholic steatohepatitis or chemotherapy, but is not limited thereto.

The *Leuconostoc citreum* strain included in the composition according to the present invention may exist as live or dead cells, and may also exist in a dried or freeze-dried form. In addition, a culture of the *Leuconostoc citreum* strain may be an active ingredient, and the culture may include a live cell culture medium or a dead cell supernatant. Types of lactic acid bacteria suitable to be included in various compositions and formulation methods are well known to those skilled in the art.

The composition may be administered orally or parenterally. In the case of parenteral administration, the composition may be administered by intravenous injection, subcutaneous injection, intramuscular injection, intraperitoneal injection, intradermal administration, topical administration, intranasal administration, intrapulmonary administration, intrarectal administration, etc., and preferably intravenous injection, but it is not limited thereto.

A suitable dose of the composition may be variously prescribed by factors, such as a formulation method, an administration type, age, weight, and sex of a patient, a pathological condition, food, an administration time, an administration route, an excretion rate, and response susceptibility.

When the composition of the present invention is used as a pharmaceutical composition, the pharmaceutical composition of the present invention may be prepared by using pharmaceutically suitable and physiologically acceptable adjuvants in addition to the active ingredients. As the adjuvants, excipients, disintegrants, sweeteners, binders, coating agents, expanding agents, lubricants, slip modifiers, flavoring agents, or the like may be used.

The pharmaceutical composition may be preferably formulated by further including at least one kind of pharmaceutically acceptable carrier in addition to the above-described active ingredients for administration.

For example, for formulation in the form of tablets or capsules, the active ingredient may be combined with an oral, a non-toxic pharmaceutically acceptable inert carrier such as ethanol, glycerol, water, or the like. Further, if desired or necessary, suitable binders, lubricants, disintegrants and coloring agents may also be included as a mixture. The suitable binders are not limited thereto, but include natural sugars such as starch, gelatin, glucose or beta-lactose; natural and synthetic gums such as acacia, tragacanth or sodium oleate; sodium stearate, magnesium stearate, sodium benzoate, sodium acetate, sodium chloride and the like. The disintegrant is not limited thereto, but includes starch, methylcellulose, agar, bentonite, xanthan gum, or the like. In the composition formulated with a liquid solution, the pharmaceutically acceptable carrier is suitable for sterilized and living bodies and may use saline, sterilized water, ringer's solution, buffered saline, albumin injection solution, dextrose solution, maltodextrin solution, glycerol, ethanol, and a mixture of at least one of these ingredients, and if necessary, may add other general additives such as antioxidants, buffers, and bacteriostatic agents. In addition, the composition may be prepared in injectable formulations such as aqueous solutions, suspensions, and emulsions, pills, capsules, granules, or tablets by further adding a diluent, a dispersant, a surfactant, a binder, and a lubricant.

Furthermore, as a suitable method in the field, the composition may be formulated preferably according to each disease or ingredient using a method disclosed in Remington's Pharmaceutical Science, Mack Publishing Company, Easton PA.

A composition including a *Leuconostoc citreum* strain of the present invention or its culture as an active ingredient may be used as a food composition or food additive composition for preventing or improving intestinal damage.

The food composition may be a health functional food form.

The "functional health food" refers to food prepared and processed using raw materials or ingredients that have functionality useful to the human body in accordance with the Health Functional Food Act (Article 3 (1)), and the "functionality" means regulating nutrients for the structure and function of the human body or obtaining useful effects for health uses such as physiological functions (Article 3 (2)).

The food composition may further include a food additive, and compliance as the "food additive" is determined by the specifications and standards for the corresponding item in accordance with the General Rules of the Korea Food Additives Code and general test methods approved by the Ministry of Food and Drug Safety, unless otherwise specified.

The items disclosed in the "Korea Food Additives Code" may include, for example, chemical composites such as ketones, glycine, potassium citrate, nicotinic acid, and cinnamic acid; natural additives such as persimmon pigment, licorice extract, crystalline cellulose, and guar gum; mixed formulations such as sodium L-glutamate formulations, noodle-added alkali agents, preservative formulations, tar color formulations, etc.

Foods containing the active ingredient of the present invention may include confectionery such as bread, rice cakes, dried confectionery, candy, chocolate, chewing gum, and jam; ice cream products such as ice cream, frozen confectionery, and ice cream powder; dairy products such as milk, low-fat milk, lactose-degraded milk, processed milk, goat milk, fermented milk, butter milk, concentrated milk, milk cream, butter milk, natural cheese, processed cheese, powdered milk, and whey; meat products such as processed meat products, processed egg products, and hamburgers; fish meat products such as fish cake, ham, sausage, bacon, etc.; noodles such as ramen, dried noodles, fresh noodles, fried noodles, deluxe dried noodles, improved soft noodles, frozen noodles, and pasta; drinks such as fruit drinks, vegetable drinks, carbonated drinks, soy milk, *Lactobacillus* drinks such as yogurt, and mixed drinks; seasoned foods such as soy sauce, soybean paste, gochujang, chunjang, cheongguk-jang, mixed soy sauce, vinegar, sauces, tomato ketchup, curry, and dressing; margarine, shortening and pizza, but are not limited thereto.

In addition, the composition of the present invention may include various nutrients, vitamins, electrolytes, flavoring agents, coloring agents, pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, or the like. In addition, the composition of the present invention may include pulps for preparing natural fruit juices, fruit juice beverages or vegetable beverages. These ingredients may be used independently or in combination.

The beverage composition including the active ingredient of the present invention is not particularly limited in other ingredients, and may contain various flavoring agents, natural carbohydrates, or the like as additional ingredients like conventional beverages. Examples of the above-mentioned natural carbohydrates may include general sugars, such as monosaccharides (e.g., glucose, fructose and the like); disaccharides (e.g., maltose, sucrose and the like); and polysaccharides (e.g., dextrin, cyclodextrin and the like), and sugar alcohols such as xylitol, sorbitol, erythritol, and the like. As flavoring agents other than those described above, natural flavoring agents (thaumatin, stevia extract (e.g., Rebaudioside A, glycyrrhizin etc.)) and synthetic flavoring agents (saccharin, aspartame, etc.) may be advantageously used.

Further, a composition including a *Leuconostoc citreum* strain of the present invention or its culture as an active ingredient may be used as a feed composition or feed additive composition for preventing or improving livestock intestinal damage.

When the composition is prepared as a feed additive, the composition may be prepared in the form of 20 to 90% high-concentrate or powder or granules. The feed additive may further include any one or one or more of organic acids such as citric acid, fumaric acid, adipic acid, lactic acid, and malic acid, phosphates such as sodium phosphate, potassium phosphate, acidic pyrophosphate, and polyphosphate, or natural antioxidants such as polyphenol, catechin, alpha-tocopherol, rosemary extract, vitamin C, green tea extract, licorice extract, chitosan, tannic acid, phytic acid, and the like. When prepared as a feed, the composition may be formulated in a conventional feed form, and may include general feed ingredients together.

The feed and the feed additives may further include grains, such as milled or ground wheat, oats, barley, corn and rice; vegetable protein feeds, such as feeds based on rape, soybean, and sunflower as a main ingredient; animal protein feeds, such as blood meal, meat meal, bone meal and fish meal; sugar and dairy products, such as dry ingredients consisting of various powdered milk and whey powder, and in addition, nutritional supplements, digestion and absorption enhancers, growth promoters, and the like may be further included.

The feed additive may be administered to animals alone or also administered in combination with other feed additives in an edible carrier. In addition, the feed additives may be easily administered to animals as a top dressing, directly mixed with animal feed, or in an oral formulation separate from feed. When the feed additive is administered separately from animal feed, the feed additive may be prepared as an immediate release or sustained release formulation in combination with a pharmaceutically acceptable edible carrier, as well-known in the art. Such edible carriers may be solids or liquids, for example corn starch, lactose, sucrose, soybean flakes, peanut oil, olive oil, sesame oil and propylene glycol. When the solid carrier is used, the feed additive may be tablets, capsules, powder, troches or sugar-containing tablets or microdispersible top dressing. When the liquid carrier is used, the feed additive may be formulations of gelatin soft capsules, syrups, suspensions, emulsions, or solution formulations.

In addition, the feed and the feed additive may contain auxiliary agents, such as preservatives, stabilizers, wetting agents or emulsifying agents, solution accelerators, and the like. The feed additive may be used to be added to an animal feed by steeping, spraying or mixing.

The feed or feed additive of the present invention may be applied to a plurality of animal diets including mammals, poultry and fish.

The mammals may be used for pigs, cows, horses, sheep, rabbits, goats, rats, hamsters, and guinea pigs, which are rodents and laboratory rodents, as well as pets (e.g., dogs and cats). The poultry may also be used for chickens, turkeys, ducks, geese, pheasants, and quails. The fish may be used for carp, crucian carp, trout, etc., but the present invention is not limited thereto.

Modes

Hereinafter, the present invention will be described in more detail through Examples. These Examples are to explain the present invention in more detail, and it will be apparent to those skilled in the art that the scope of the present invention is not limited by these Examples in accordance with the gist of the present invention.

Example 1. Culture of Strain

A *Leuconostoc citreum* WiKim0104 (accession number KCCM12420P) strain was distributed with the permission of the depositor, Korea Food Research Institute, and experiments were conducted.

The distributed *Leuconostoc citreum* WiKim0104 strain was inoculated at 1% in 30 ml of an MRS liquid medium and static cultured at 30° C. for 18 hours. After incubation, the culture solution was stored separately by centrifugation at 3000 rpm for 10 minutes, and the cells were washed three times with a phosphate buffered saline (PBS) solution to remove the remaining medium component.

Example 2. Confirmation of Effect of Enhancing Expression of Genes Related to Barrier Maintenance in Enterocytes For culture of enterocytes (HT29 cells and Caco2), an RPMI medium supplemented with penicillin/streptomycin and 10% FBS was used and a 6-well plate transwell was used and prepared.

After culturing enterocytes until growing confluently, the medium was replaced with 200 μl of a new medium containing 1 μg/ml of LPS and 500 μM of palmitic acid. At this time, the prepared *Leuconostoc citreum* WiKim0104 strain was treated at a concentration of $1 \times 10^8$ CFU/mL. After the strain was treated and cultured for 24 hours, the cells were washed three times with PBS, harvested, and RNA was isolated using a TRIZOL reagent. FIG. 1 illustrated a result of synthesizing cDNA from 1 μg of RNA using a cDNA synthesis kit and then confirming the expression level of ZO-1, a tight junction-related gene, by a quantitative real time polymerase chain reaction (qRT-PCR) method.

As illustrated in FIG. 1, the ZO1 expression level decreased by LPS and palmitic acid was recovered in a *Leuconostoc citreum* WiKim0104 strain treatment group.

Example 3. Confirmation of Barrier Maintenance Efficacy in Non-Alcoholic Steatohepatitis Model Non-alcoholic steatohepatitis was also known to be closely related to dysfunction of tight junction. Accordingly, after treatment with the composition according to the present invention in a non-alcoholic steatohepatitis model induced by a choline deficient high fat diet (CDHFD) method, the expression levels of genes related to tight junction were measured. 6 to 8-week-old C57BL6 mice ingested the composition by a CDHFD method for 8 weeks to induce non-alcoholic steatohepatitis and then fed a *Leuconostoc citreum* WiKim0104 strain 5 days a week at a concentration of $2 \times 10^9$ CFU/day for 12 weeks. After 12 weeks, the results of confirming the expression levels of Occludin and ZO1, which were tight junction-related genes, in the intestinal tissues of a control group and an experimental group were illustrated in FIGS. 2 and 3.

As shown in FIGS. 2 and 3, it was confirmed that the expression levels of the Occludin and ZO1 protein genes were restored to a normal group level in the group ingested with the *Leuconostoc citreum* Wikim0104 strain.

The invention claimed is:

1. A method for treating intestinal damage related to dysfunction of tight junction, the method comprising administering a composition comprising a *Leuconostoc citreum* WiKim0104 strain having accession number KCCM12420P and having the nucleic acid sequence of SEQ ID NO: 1 or a culture comprising the *Leuconostoc citreum* WiKim0104 strain as an active ingredient to a subject in need thereof, wherein the intestinal damage is caused by inflammatory bowel disease or chemotherapy.

2. The method of claim 1, wherein the composition is administered via oral administration or parenteral administration.

3. The method of claim 2, wherein the parenteral administration method is intravenous injection, subcutaneous injection, intramuscular injection, intraperitoneal injection, intradermal administration, topical administration, intranasal administration, intrapulmonary administration or intrarectal administration.

* * * * *

SEQUENCE LISTING

```
<160> NUMBER OF SEQ ID NOS: 1

<210> SEQ ID NO 1
<211> LENGTH: 1430
<212> TYPE: DNA
<213> ORGANISM: Leuconostoc citreum

<400> SEQUENCE: 1
gatgaacgct ggcggcgtgc ctaatacatg caagtcgaac gcgcagcgag aggtgcttgc      60
acctttcaag cgagtggcga acgggtgagt aacacgtgga taacctgcct caaggctggg     120
gataacattt ggaaacagat gctaataccg aataaaactt agtatcgcat gatatcaagt     180
taaaaggcgc tacggcgtca cctagagatg gatccgcggt gcattagtta gttggtgggg     240
taaaggctta ccaagacgat gatgcatagc cgagttgaga gactgatcgg ccacattggg     300
actgagacac ggcccaaact cctacgggag gctgcagtag ggaatcttcc acaatgggcg     360
caagcctgat ggagcaacgc cgcgtgtgtg atgaaggctt tcgggtcgta aagcactgtt     420
gtatgggaag aaatgctaaa atagggaatg attttagttt gacggtacca taccagaaag     480
ggacggctaa atacgtgcca gcagccgcgg taatacgtat gtcccgagcg ttatccggat     540
ttattgggcg taaagcgagc gcagacggtt gattaagtct gatgtgaaag cccggagctc     600
aactccggaa tggcattgga aactggttaa cttgagtgtt gtagaggtaa gtggaactcc     660
atgtgtagcg gtggaatgcg tagatatatg gaagaacacc agtggcgaag gcggcttact     720
ggacaacaac tgacgttgag gctcgaaagt gtgggtagca aacaggatta gatacctgg     780 tagtccacac cgtaaacgat gaatactagg tgttaggagg tttccgcctc ttagtgccga     840
agctaacgca ttaagtattc cgcctgggga gtacgaccgc aaggttgaaa ctcaaaggaa     900
ttgacgggga cccgcacaag cggtggagca tgtggtttaa ttcgaagcaa cgcgaagaac     960
cttaccaggt cttgacatcc tttgaagctt ttagagatag aagtgttctc ttcggagaca    1020
aagtgacagg tggtgcatgg tcgtcgtcag ctcgtgtcgt gagatgttgg gttaagtccc    1080
gcaacgagcg caacccttat tgttagttgc cagcattcag ttgggcactc tagcgagact    1140
gccggtgaca aaccggagga aggcgggac gacgtcagat catcatgccc cttatgacct    1200
```

-continued

```
gggctacaca cgtgctacaa tggcgtatac aacgagttgc caacctgcga aggtgagcta    1260
atctcttaaa gtacgtctca gttcggactg cagtctgcaa ctcgactgca cgaagtcgga    1320
atcgctagta atcgcggatc agcacgccgc ggtgaatacg ttcccgggtc ttgtacacac    1380
cgcccgtcac accatgggag tttgtaatgc ccaaagccgg tggcctaacc             1430
```